US00PP11209P

United States Patent [19]

VandenBerg

[11] Patent Number: Plant 11,209

[45] Date of Patent: Feb. 8, 2000

[54] CHRYSANTHEMUM PLANT NAMED 'YOLANSING'

[75] Inventor: Cornelis P. VandenBerg, Salinas, Calif.

[73] Assignee: Yoder Brothers, Inc., Barberton, Ohio

[21] Appl. No.: 09/112,233

[22] Filed: Jul. 9, 1998

[51] Int. Cl.[7] ..... A01H 5/00

[52] U.S. Cl. ..... Plt./287

[58] Field of Search ..... Plt./287

[56] References Cited

U.S. PATENT DOCUMENTS

P.P. 6,552 1/1989 Hesse ..... Plt./287

P.P. 7,585 7/1991 VandenBerg ..... Plt./287

*Primary Examiner*—Howard J. Locker

*Attorney, Agent, or Firm*—C. A. Whealy

[57] ABSTRACT

A distinct cultivar of Chrysanthemum plant named 'Yolansing', characterized by its upright and uniformly mounded plant habit; freely branching habit; large leaves; uniform and early flowering; large decorative disbud-type inflorescences that are about 11.5 cm in diameter; attractive lavender-colored ray florets; and excellent postproduction longevity with inflorescences and leaves maintaining good substance and color for about four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yolansing. The plant is being marketed under the name Lansing.

The new Chrysanthemum is a product of a planned breeding program conducted by the inventor in Salinas, Calif. The objective of the breeding program is to create new pot-type Chrysanthemum cultivars having desirable inflorescence forms and floret colors and excellent post-production longevity.

The new Chrysanthemum originated from a cross made by the breeder in October, 1993, in Salinas, Calif., of an unnamed proprietary Chrysanthemum seedling selection as the male, or pollen, parent with the commercial Chrysanthemum cultivar Boaldi (disclosed in U.S. Plant Pat. No. 6,613) as the female, or seed, parent.

The new Chrysanthemum was discovered and selected by the inventor as a flowering plant within the progeny of the stated cross in a controlled environment in Salinas, Calif., in December, 1994. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of the new Chrysanthemum are stable and reproduced true to type in successive generations.

SUMMARY OF THE INVENTION

The cultivar Yolansing has not been observed under all possible environmental conditions. The phenotype may vary somewhat with variation in environment such as temperature, daylength and light intensity, without, however, any variance in genotype.

The following traits have been repeatedly observed and are determined to be the unique characteristics of 'Yolansing'. These characteristics in combination distinguish 'Yolansing' as a new and distinct Chrysanthemum:

1. Upright and uniformly mounded plant habit.

2. Freely branching habit, dense plants.

3. Large leaves.

4. Uniform and early flowering.

5. Large decorative disbud-type inflorescences that are about 11.5 cm in diameter.

6. Attractive lavender-colored ray florets.

7. Excellent postproduction longevity with inflorescences and leaves maintaining good substance and color for about four weeks in an interior environment.

The new Chrysanthemum can be compared to the Chrysanthemum cultivar Charm (disclosed in U.S. Plant Pat. No. 5,502). However in side-by-side comparisons in Salinas, Calif., and Leamington, Ontario, Canada, under commercial practice, plants of the new Chrysanthemum differed from plants of the cultivar Charm in the following characteristics:

1. Plants of the new Chrysanthemum are taller than plants of the cultivar Charm.

2. Plants of the new Chrysanthemum are more freely branching than plants of the cultivar Charm.

3. Ray florets of plants of the new Chrysanthemum are darker in color than ray florets of plants of the cultivar Charm.

BRIEF DESCRIPTION OF THE PHOTOGRAPHS

The accompanying color photographs illustrate the overall appearance of the new Chrysanthemum showing the colors are true as it is reasonably possible to obtain in colored reproductions of this type.

The photograph at the top of the first sheet comprises a top perspective view of a typical flowering plant of 'Yolansing'. The photograph at the bottom of the first sheet is a close-up view of a typical inflorescence of a plant of 'Yolansing'.

The photograph on the second sheet is a close-up view of a typical leaf and inflorescence of a plant of 'Yolansing'. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under greenhouse conditions which approximate those generally used in commercial potted Chrysnthemum production. Four unrooted cuttings were directly stuck in a 15-cm container and pinched once. Measurements and numerical values represent averages of typical flowering plants.

Botanical classification: *Dendranthema grandiflora* cultivar Yolansing.

Commercial classification: Decorative disbud-type pot chrysanthemum.

Parentage:

*Male or pollen parent.*—Unnamed proprietary *Dendranthema grandiflora* seedling selection.

*Female or seed parent.*—*Dendranthema grandiflora* cultivar Boaldi (U.S. Plant Pat. No. 6,613).

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative disbud-type pot Chrysanthemum. Upright, inverted triangle. Stems initially upright, then somewhat spreading giving a uniformly mounded appearance to the plant. Freely branching; about five lateral branches develop after removal of terminal apex (pinching), dense and full plants.

*Plant height.*—Medium, about 26 cm.

*Plant width.*—About 38 cm.

*Stem color.*—144A.

*Foliage description.*—Arrangement: Alternate. Length: About 8.5 cm. Width: About 7 cm. Apex: Mucronate. Base: Atternate. Margin: Palmately lobed, sinuses between lateral lobes diverging. Texture: Upper and lower surfaces slightly pubescent, very fine white hairs. Veins prominent on lower surface. Petiole length: About 1.5 cm. Color: Young foliage upper surface: Close to 147A. Young foliage lower surface: Close to 147B. Mature foliage upper surface: Close to 147A. Mature foliage lower surface: Close to 147B. Venation upper surface: 147A to 147B. Venation lower surface: 147B.

Inflorescence description:

*Appearance.*—Decorative disbud-type inflorescence form with elongated oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about eight weeks later.

*Postproduction longevity.*—Inflorescences and leaves will maintain good color and substance for about four weeks in an interior environment.

*Quantity of Inflorescences.*—As a disbud-type, all flowering stems are removed but one to maximize inflorescence size. About five inflorescences per plant.

*Inflorescence bud.*—Height: About 6 mm. Diameter: About 8 mm. Color: Darker than 144A.

*Inflorescence size.*—Diameter: About 11.5 cm. Depth (height): About 2.5 cm. Diameter of disc: About 8 mm, inconspicuous.

*Ray florets.*—Shape: Elongated oblong with very short corolla tube. Aspect: Straight, flat to convex. Length: About 5.75 cm. Width: About 1.25 cm. Apex: Mostly acute. Margin: Entire. Texture: Smooth, glabrous, iridescent. Number of ray florets per inflorescence: About 212. Color: When opening, upper surface: 77A. When opening, lower surface: 77A to 77B. Fully opened, upper surface: Close to 77B to 75A. Fully opened, lower surface: 77C to 77D.

*Disc florets.*—Shape: Tubular. Apex: Dentate. Length: About 7 mm. Width: Apex: About 1 mm. Base: About 0.5 mm. Number of disc florets per inflorescence: Few, about 25. Color: Immature: 154A. Mature: Apex: 15A. Mid-section and base: White to light green.

*Reproductive organs.*—Androecium: Present on disc florets only. Anther color: 13A. Pollen: Amount: Moderate. Color: 21A. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Yolansing', as illustrated and described.

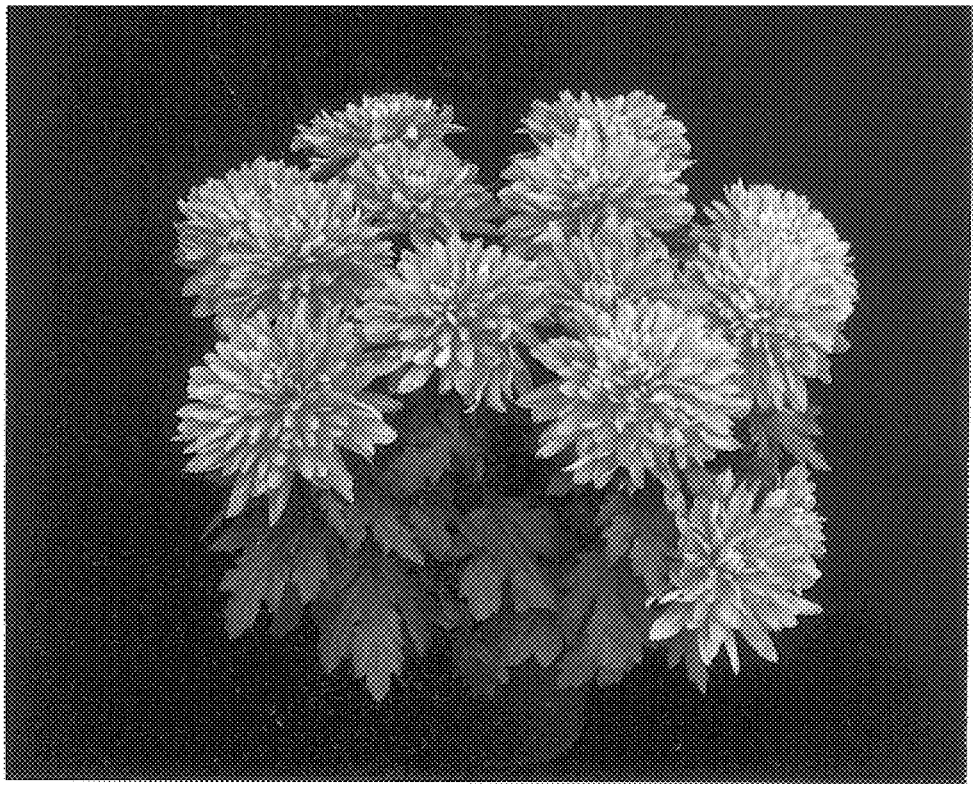
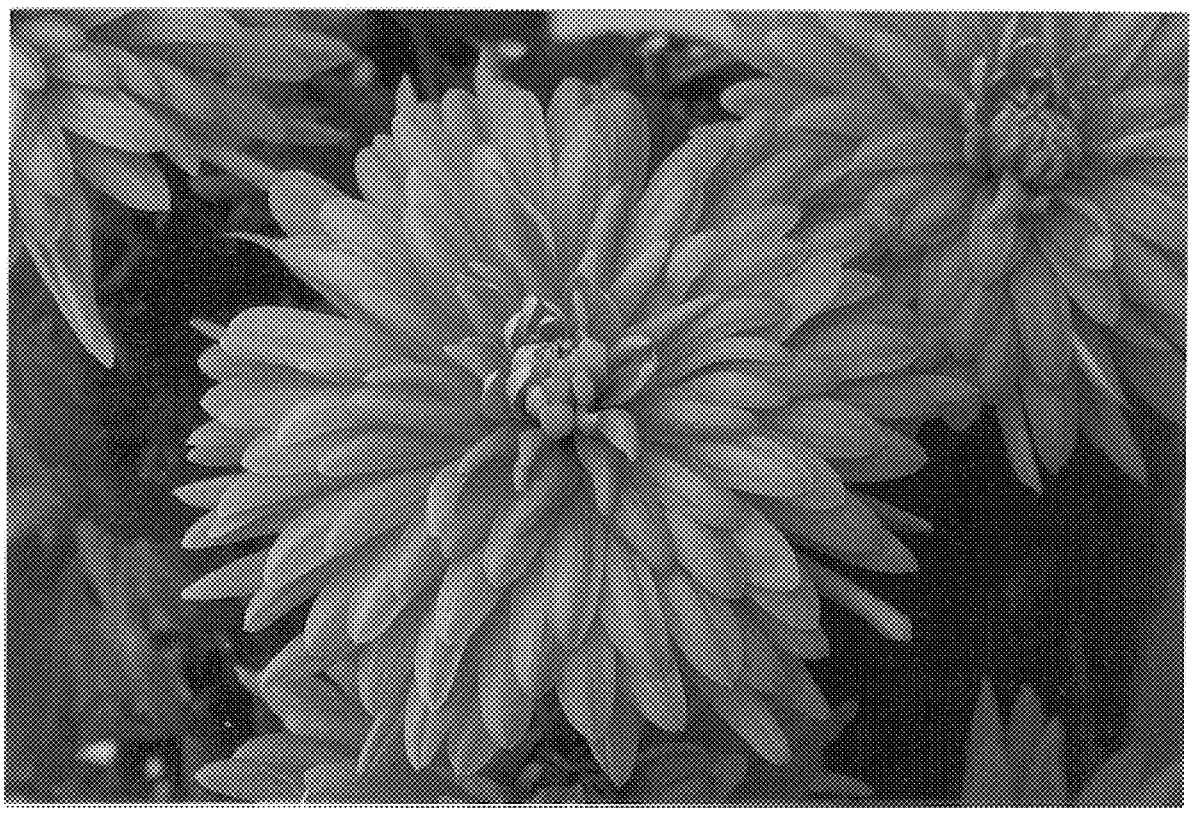

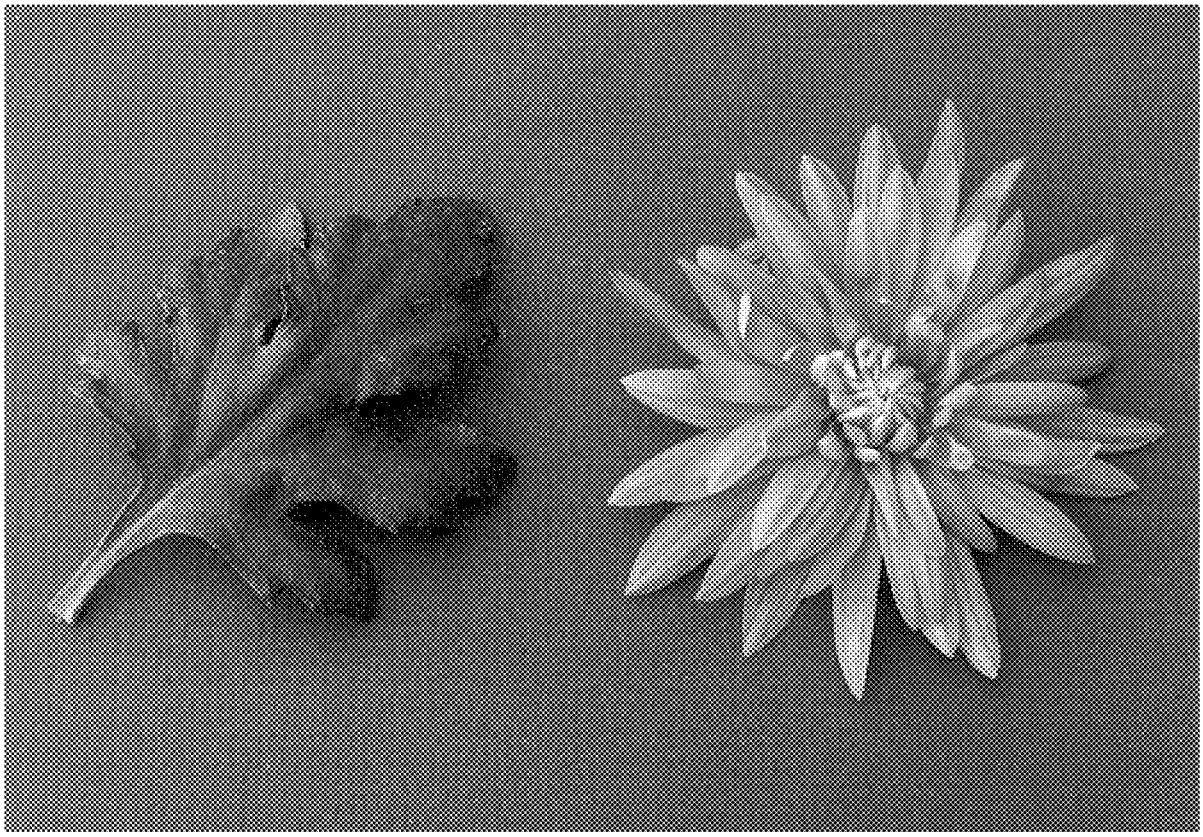

* * * * *